(12) United States Patent
Irvin et al.

(10) Patent No.: US 7,544,811 B1
(45) Date of Patent: *Jun. 9, 2009

(54) DI- AND MULTIFUNCTIONAL MONOMERS FOR PRODUCING TETRAZOLE BASED POLYMERS

(75) Inventors: David J. Irvin, Ridgecrest, CA (US); Mark H. Mason, Inyokern, CA (US); Stephen Fallis, Ridgecrest, CA (US); Andrew Chafin, Ridgecrest, CA (US)

(73) Assignee: The United States of America as represented by the Secretary of the Navy, Wahsington, DC (US)

( * ) Notice: Subject to any disclaimer, the term of this patent is extended or adjusted under 35 U.S.C. 154(b) by 394 days.

This patent is subject to a terminal disclaimer.

(21) Appl. No.: 11/151,189

(22) Filed: May 27, 2005

(51) Int. Cl.
*C07D 257/04* (2006.01)
(52) U.S. Cl. .................................................... 548/251
(58) Field of Classification Search .................. 548/251
See application file for complete search history.

(56) References Cited

U.S. PATENT DOCUMENTS 4,849,466 A * 7/1989 Michaelis .................... 524/105

* cited by examiner

*Primary Examiner*—Rebecca L Anderson
*Assistant Examiner*—Shawquia Young
(74) *Attorney, Agent, or Firm*—Brian F. Drazich; Charlene A. Haley

(57) ABSTRACT

The present invention discloses monomers of structure (IV) wherein "X" is an alkyl, aryl, or oligoether group, and

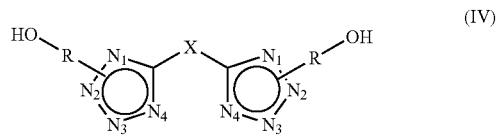

"R" is an alkyl, aryl, or oligoether group that is chemically bonded to the $N_1$ or $N_2$ position of each of the tetrazole rings. The monomers of the present invention are suitable as binders in energetic compositions.

24 Claims, No Drawings

DI- AND MULTIFUNCTIONAL MONOMERS FOR PRODUCING TETRAZOLE BASED POLYMERS

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND OF THE INVENTION

There is a need for novel energetic binders to increase the performance of pyrotechnics, gun propellants, rocket propellants, air-bag gas generator propellants, and explosives. Depending on the application, these materials are typically 3-25% binder by mass. Therefore, improvements to the energy content, mechanical properties, or insensitive munitions properties of the polymeric binder can have significant affects on the performance of the energetic material in question.

In general many pyrotechnics, propellants, explosives are comprised of a polymeric binder that holds one or more energetic solids in a plastic matrix. The polymeric binder serves many roles in these materials. Initially the polymer can aid in processing. In fact, the properties of the polymer will significantly affect how a material is processed, whether it is cast or pressed or extruded. Furthermore, the polymer mechanically holds all the ingredients together, serving as a structural element literally binding together the final material. This role is especially critical in rocket propellants, because cracks and voids in the propellant will lead to motor grain failure, often with catastrophic results. The binder serves many safety functions. The binder physically coats the energetic solids in these materials, this provides a physical buffer to minimize the physical and chemical interaction of reactive solids with each other. This generally lowers the electrostatic discharge, impact, and friction sensitivity of the final material. In some materials, especially rocket propellants, the binder also serves as a fuel when the hydrocarbon polymer is combusted by the oxidizer. However, the binder generally diminishes the performance (detonation pressure and velocity) of most explosives. To improve the performance of explosives with significant binder content, and to increase the energy density of propellants energetic polymers are needed.

While there are energetic binders available (polyglycidyl nitrate (PGN), polyglycidyl azide (GAP), azidomethyl-methyl-oxetane (AMMO), bis((azido-methyl)oxetane) (BAMMO), nitratomethyl-methyloxetane (NMMO), etc.) the safety benefits of increasing binder content are lost because these materials contain either organic azides or nitrate esters (or both). These functional groups are chemically unstable, easily ignited, and generally create reactive fragments on aging. In fact, propellants that utilize nitrate esters generally require expensive monitoring programs throughout their life cycle to insure both adequate safety properties and performance as the propellant ages. The cost of such monitoring is often cited as one reason most modern explosives do not to use nitrate esters as binder materials. Furthermore, the energetic groups are pendant moieties attached to the polymer, but not incorporated into the polymer backbone. This impairs the physical properties of these polymers and causes the formulator to need a higher weight percent of binder in order to achieve adequate coating. In short, there is a need for improved energetic binders to address safety, performance, aging, and processing requirements.

While tetrazoles are somewhat less energetic than azides or nitrates, the bis-alkyltetrazoles of interest are more thermally stable and substantially less chemically reactive. Higher percentages of these binders could be used without anticipating negative safety consequences. Furthermore, the energetic functionality is built into the polymer backbone, minimizing the total moles of pendant atoms. This is anticipated to yield a binder with superior physical properties. A dihydroxy-terminated bis-tetrazole (2,2 Bis((2-ethanol)-1 or 2H-tetrazole)-propane or BETP) has been synthesized on the multigram scale. Initial differential scanning calorimetry (DSC) analysis shows this pre-polymer has promise as an energetic cured urethane binder for explosives and propellants and gas generatos.

U.S. Pat. No. 5,053,086 issued on Oct. 1, 1991 to Henry, et al., which teaches gas generating compositions containing energetic high nitrogen such as ammonium 5-nitraminotetrazole and 5,5'-bitetrazole. This work yielded polymeric binders that are too rigid and "glassy" for the intended application. The chemical structure of the present invention polymers builds more flexibility into the backbone, yielding improved elastomers. Further research by Demko teaches the addition of sodium azide to nitrites to give 1H-tetrazoles in water with zinc salts as catalysts. (Demko, Z. P.; Sharpless, K. B. "Preparation of 5-substituted 1H-tetrazoles from nitrites in water." *J. Org. Chem.* 2001, 66, 7945). This step is only one method to obtain the tetrazole intermediate. Further reaction is necessary to produce the alcohol-based monomers. The addition of the alkyl alcohol is two fold: first, the short alkyl chain adds flexibility, solubility; second, the alcohol group allows for the production of stable polyurethanes. Polymerization of the tetrazole would produce the less stable polyurea.

Tetrazole compounds have application in many fields including, but not limited to, chemistry, ligands, metabolically stable surrogate for a carboxylic acid group, and material sciences including explosives and propellants and air bag gas generators.

It is to be understood that the foregoing general description and the following detailed description are exemplary and explanatory only and are not to be viewed as being restrictive of the present invention, as claimed. Further advantages of this invention will be apparent after a review of the following detailed description of the disclosed embodiments and in the appended claims.

DETAILED DESCRIPTION OF THE INVENTION

Embodiments of the present invention generally relate to a monomer having the general structure (1) comprising: wherein [n] is a value of 2 to 9; wherein [X] comprises at least one group

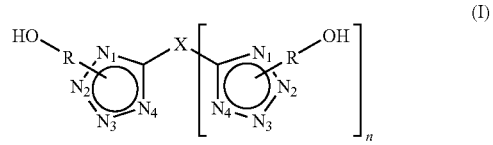

of alkyls, aryls, and oligoethers; and wherein [R] comprises at least one group of alkyls, aryls, and oligoethers, wherein [R] is chemically bonded to $N_1$ or $N_2$ position.

The monomer produced is a multifunctional monomer including at least one general structure of tri-tetrazole polyol, tetra-tetrazole polyol, penta-tetrazole polyol, and hexa-tetrazole polyol.

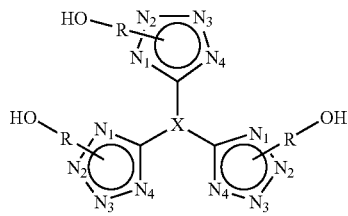

General structure of trifunctional monomer

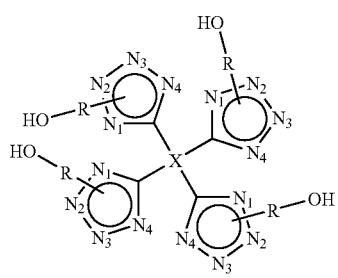

General structure of tetrafunctional monomer

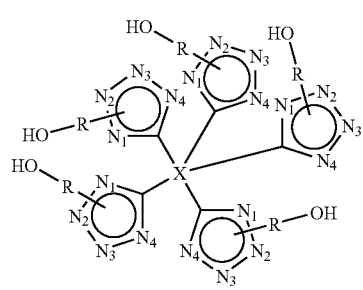

General structure of pentafunctional monomer

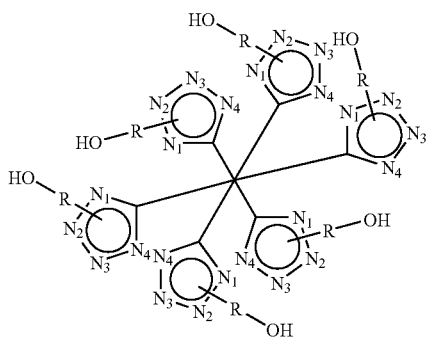

General structure of hexafunctional monomer

In other embodiments, the monomer (I) is produced by the process, including an effective

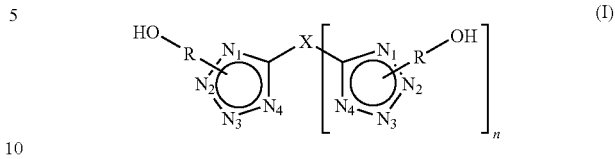

amount of nitrile(s) reacting with inorganic azide and a divalent zinc salt in a first solvent at a temperature in the range of about 70° C. to about 170° C. for a time period in the range of about 1 to 24 hours, wherein the nitrile(s) having the general structure (II); wherein [n] of the nitrile(s) is

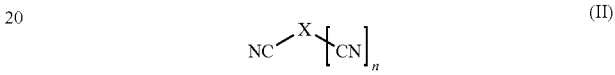

2-9, wherein [X] comprises at least one group of alkyls, aryls, and oligoethers and cooling to room temperature producing poly tetrazole having the general structure (III), wherein [H] is chemically bonded to $N_1$ or $N_2$ position, wherein [X] comprises at least one group of alkyls, aryls, and oligoethers, wherein [n] is 2-9; the poly tetrazole purified by recrystallization in a second solvent;

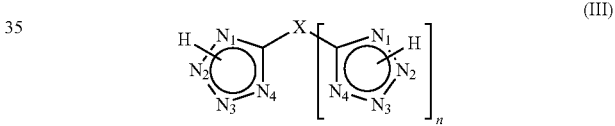

and an effective amount of said purified poly tetrazole reacting with a third solvent, a soluble reversible or non-reversible base, and 2-chloro-ethanol at a temperature in the range of about 70° C. to about 150° C. for a time period in the range of about 1 to about 10 hours, cooling to room temperature producing tetrazole polyol having the general structure (I), wherein [R] comprises at least one group of alkyls, aryls, and oligoethers, wherein [R] is chemically bonded to $N_1$ or $N_2$ position, wherein [X] comprises at least one group of alkyls, aryls, and oligoethers, wherein [n] is a value of 2 to 9.

When the process utilizes nitrile(s), the nitrile(s) include, but not limited to, at least one of tricyanomethane, tetracyanopropane, pentacyanopropane, and hexacyanopropane. When tetracyanopropane is utilized it includes at least 1,1,3,3-tetracyanopropane. In embodiments, the inorganic azide includes at least one of sodium azide, lithium azide, and potassium azide. In the method for making tetrazole diols, the divalent salts utilized include, but not limited to, at least zinc bromide. The first solvent is polar which includes at least one of water, alcohol including 2-propanol, dimethylformanide, dimethylacetamide, and N-methylpyrrolidinone. The second solvent includes at least one of ethyl acetate and hexane. The third solvent is polar which includes at least one of water, alcohol including 2-propanol, dimethylformanide, dimethylacetamide, and N-methyl pyrrolidinone. In embodiments of the present invention, a soluble base is utilized. The soluble reversible base includes at least one of sodium hydroxide, lithium hydroxide, and potassium hydroxide. The soluble non-reversible base includes at least one of sodium hydride, lithium hydride, and potassium hydride.

Further embodiments of the present invention include a monomer having the general structure (IV) comprising: wherein [X] comprises at least one group of alkyls, aryls, and

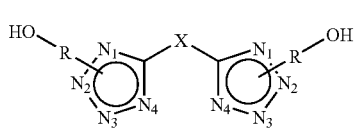

(IV)

oligoethers; and wherein [R] comprises at least one group of alkyls, aryls, and oligoethers, wherein [R] is chemically bonded to $N_1$ or $N_2$ position.

The monomers in this embodiment are di-functional monomers having the general structure di-tetrazole diol. The di-tetrazole diol (IV) in this embodiment includes Bis(N-ethanol-5-tetrazolyl)propane, the Bis(N-ethanol-5-tetrazolyl)propane includes at least one of 2,2-Bis(5-(1-N-ethanol-5-tetrazolyl)propane (IVa), 2,2-Bis(5-(2-N-ethanol-5-tetrazolyl)propane (IVb), and 2-(5-(1-N-ethanol-5-tetrazolyl)-2-(5-(2-N-ethanol-5-tetrazolyl)propane (IVc).

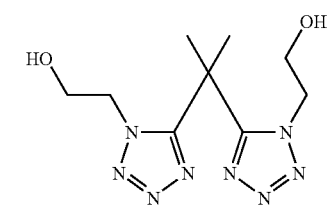

2,2-Bis(5-(1-N-ethanol-5-tetrazolyl)propane (IVa)

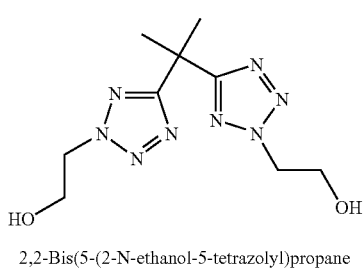

2,2-Bis(5-(2-N-ethanol-5-tetrazolyl)propane (IVb)

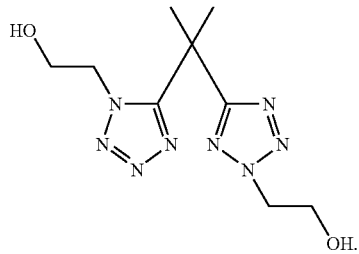

2-(5-(1-N-ethanol-5-tetrazolyl)-2-(5-(2-N-ethanol-5-tetrazolyl)propane (IVc)

The monomer in another embodiment produced is a di-tetrazole diol (IV). The di-tetrazole diol in this embodiment includes Bis(N-ethanol-5-tetrazolyl)methane, the Bis(N-ethanol-5-tetrazolyl)methane includes at least one of 2,2-Bis(5-(1-N-ethanol-5-tetrazolyl)methane (IVd), 2,2-Bis(5-(2-N-ethanol-5-tetrazolyl)methane (IVe), and 2-(5-(1-N-ethanol-5-tetrazolyl)-2-(5-(2-N-ethanol-5-tetrazolyl)methane (IVf).

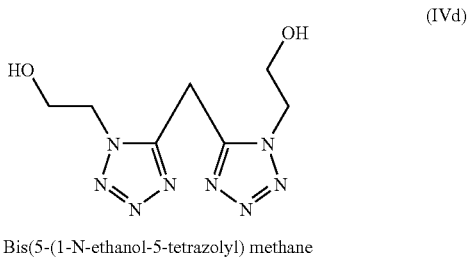

Bis(5-(1-N-ethanol-5-tetrazolyl) methane (IVd)

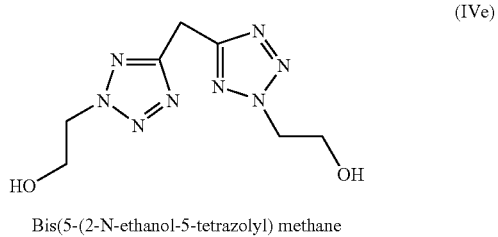

Bis(5-(2-N-ethanol-5-tetrazolyl) methane (IVe)

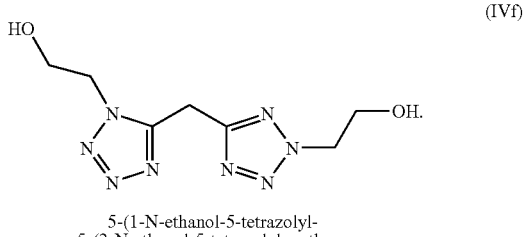

5-(1-N-ethanol-5-tetrazolyl-5-(2-N-ethanol-5-tetrazolyl methane (IVf)

When each di-tetrazole is produced it includes its isomer and each di-tetrazole isomer is independent of other di-tetrazole isomers. In embodiments of the present invention, the tetrazole diol is alkylated tetrazole diol and each alkylated tetrazole diol includes its isomers and each alkylated tetrazole isomer is independent of other alkylated tetrazole isomers. In some embodiments, the alkylated tetrazole diol includes di-tetrazole diol. In other embodiments, the tetrazole diol is arylated tetrazole diol and each arylated tetrazole diol includes its isomers and each arylated tetrazole isomer is independent of other arylated tetrazole isomers. Yet still in other embodiments, the arylated tetrazole diol includes di-tetrazole diol or an oligoether tethered diol. In other methods the tetrazole diol produces di-tetrazole diol.

A further embodiment of the present invention includes a monomer (V) produced by the process, comprising: an effective amount of nitrile(s) reacting with inorganic azide and a divalent

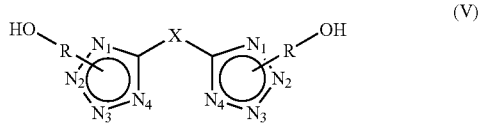

(V)

zinc salt in a first solvent at a temperature in the range of about 70° C. to about 170° C. for a time period in the range of about 1 to about 24 hours, wherein the nitrile(s) having the general structure (VI); wherein [X] comprises at least one group of alkyls, aryls, and oligoethers, cooling to room

(VI)

temperature producing a di-tetrazole having the general structure (VI), wherein [H] is chemically bonded to $N_1$ or $N_2$ of position said di-tetrazole, wherein [X] comprises at least one group of alkyls, aryls, and oligoethers; the di-tetrazole purified by recrystallization or precipitation in a second

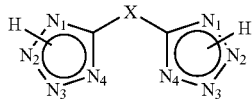

(VII)

solvent; and an effective amount of the purified di-tetrazole reacting with a third solvent, a soluble reversible or non-reversible base, and 2-chloro-ethanol at a temperature in the range of about 70° C. to about 150° C. for a time period in the range of about 1 to about 24 hours, cooling to room temperature producing a di-functional tetrazole diol having the general structure (V), wherein [X] comprises at least one group of alkyls, aryls, and oligoethers, wherein [R] comprises at least one group of alkyls, aryls, and oligoethers, wherein [R] is chemically bonded to $N_1$ or $N_2$ position of the tetrazole diol (V).

The nitrile(s) utilized include, but not limited to, at least one of dimethyl-malononitrile and malononitrile. When dimethyl-malononitrile is utilized it includes 2,2-dimethyl-malononitrile. In embodiments, the inorganic azide includes at least one of sodium azide, lithium azide, and potassium azide. In the method for making tetrazole diols, the divalent salts utilized includes zinc bromide. The first solvent is polar which includes at least one of water, alcohol including 2-propanol, dimethylformanide, dimethylacetamide, and N-methylpyrrolidinone. The second solvent includes at least one of ethyl acetate and hexane. The third solvent is polar which includes at least one of water, alcohol including 2-propanol, dimethylformanide, dimethylacetamide, and N-methyl pyrrolidinone. In embodiments of the present invention, a soluble base is utilized. The soluble reversible base includes at least one of sodium hydroxide, lithium hydroxide, and potassium hydroxide. The soluble non-reversible base includes at least one of sodium hydride, lithium hydride, and potassium hydride.

EXPERIMENTAL RESULT

In the making of tris-(hydroxyethyl-5-tetrazoyl)methane, the following is formulated. To a suspension of 1.05 gms tris-5-tetrazoylmethane (4.8 mmoles) in 25 mL water was added 0.67 gms NaOH (16.8 mmoles). This was heated to just below reflux at which time 1.0 mL 2-chloroethanol (15 mmoles) was added. The solution was refluxed overnight then cooled and concentrated in vacuum. 20 mL EtOAc was added to the residue. MeOH was then added dropwise until the gummy residue dissolves. The solids are filtered off and the filtrate was concentrated in vacuum to give 1.41 grams of a brown glass. This was taken up in 50 mL 10% MeOH/CHCl$_3$ and poured onto a short column of Silica Gel. The product was eluted using 50% MeOH/CHCl$_3$ to give 0.69 gms of a straw colored glass.

tris-5-tetrazolomethane

A solution of 1.29 grams potassium tricyanomethide (10 mmoles), 2.15 grams sodium azide (33 mmoles) and 6.76 grams zinc bromide (30 mmoles) in 50 mL H$_2$O was refluxed overnight then cooled and filtered. The solids were washed with water and dried to give 3.52 grams of a brown solid. This was stirred with 50 mL 4N HCl for 18 hours then filtered and dried to give 1.21 grams of a tan solid. This was dissolved in 25 mL 1M NaOH. The solution was filtered and the filtrate was neutralized with 4N HCl. The solids were filtered off and washed with water then dried to give 1.07 grams of an off white solid (49%).

tris-(hydroxyethyl-5-tetrazoyl)methane

To a suspension of 1.05 gms tris-5-tetrazoylmethane (4.8 mmoles) in 25 mL water was added 0.67 gms NaOH (16.8 mmoles). This was heated to just below reflux at which time 1.0 mL 2-chloroethanol (15 mmoles) was added. The solution was refluxed overnight then cooled and concentrated in vacuum. 20 mL EtOAc was added to the residue. MeOH was then added dropwise until the gummy residue dissolves. The solids are filtered off and the filtrate was concentrated in vacuum to give 1.41 grams of a brown glass. This was taken up in 50 mL 10% MeOH/CHCl$_3$ and poured onto a short column of Silica Gel. The product was eluted using 50% MeOH/CHCl$_3$ to give 0.69 gms of a straw colored glass.

Example of Tetra-Functional 1,1,3,3-tetra-5-tetrazolopropane

In a glass vial equipped with a stir bar, 1,1,3,3-tetracyanopropane (1.0 g), sodium azide (2.0 g), zinc bromide (6.2 g), and dimethylacetamide (35 ml) were combined and were heated at 100° C. After 24 hours, the solution was added to 300 ml of water. The yellow precipitate was collected via suction filtration. The resulting solid was dried under vacuum 1,1,3,3-tetra(hydroxyethyl-5-tetrazolyl)propane A solution of 0.50 gms 1,1,3,3-tetrakis(5-tetrazolyl)propane (1.6 mmoles) and 0.26 gms NaOH (6.0 mmoles) in 20 mL water was heated to reflux while 0.51 gms 2-chloroethanol (7.6 mmoles) was added in one portion. Refluxing was continued overnight then the solution was cooled and concentrated to dryness to yield 1.24 gms of a tan glass. This was taken up in 20 mL methanol. The salts were filtered off and the filtrate concentrated in vacuum. This was then repeated to give 0.78 gms of a light tan colored glass (99%). Elemental analysis: Calc for $C_{15}H_{24}N_{20}O_4$: C 36.58%, H 4.91%, N 45.51%. Found: C 29.36%, H 4.33%, N 41.34%, C 14.78%. This works out to about 8% NaCl by weight based on the percent chlorine.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A monomer of the structure (I):

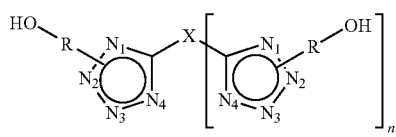

(I)

wherein "n" is a value of 2 to 9;
wherein "X" is an alkyl group; and
wherein "R" is an alkyl group, wherein "R" is chemically bonded to $N_1$ or $N_2$ position.

2. The monomer according to claim 1, wherein said monomer (I) is a multifunctional monomer which is a tri-tetrazole polyol of structure (A),

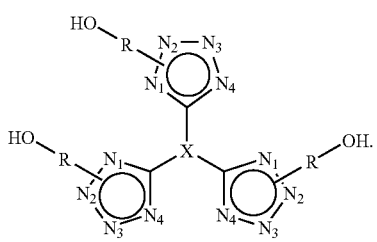

(A)

3. A process for preparing a monomer of the structure (I) comprising:

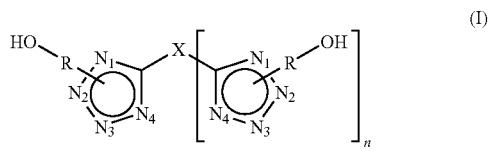

(I)

reacting an effective amount of nitrile(s) with inorganic azide and a divalent zinc salt in a first solvent at a temperature of about 70° C. to about 170° C. for about 1 hour to 24 hours, wherein said nitrile(s) are of structure (II);

(II)

wherein "n" of said nitrile(s) is 2-9, wherein "X" is an alkyl group;

cooling to room temperature to obtain a first reaction mixture containing poly tetrazole of the structure (III), wherein "H" is chemically bonded to $N_1$ or $N_2$ position, wherein "X" is an alkyl group, wherein "n" is 2-9;

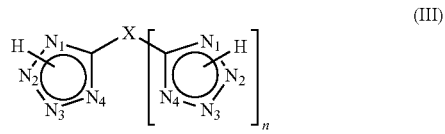

(III)

recrystallizing said poly tetrazole from a second solvent; and reacting an effective amount of said recrystallized poly tetrazole with a suitable soluble reversible or non-reversible base, and 2-chloro-ethanol in a third solvent at about 70° C. to about 150° C. for about 1 hour to about 10 hours;

cooling to room temperature to obtain a second reaction mixture containing tetrazole polyol of the structure (I), wherein "R" is an alkyl group, wherein "R" is chemically bonded to $N_1$ or $N_2$ position, wherein "X" is an alkyl group, wherein "n" is a value of 2 to 9.

4. The process according to claim 3, wherein said inorganic azide is at least one sodium azide, lithium azide, and potassium azide.

5. The process according to claim 3, wherein said divalent zinc salt is zinc bromide.

6. The process according to claim 3, wherein said first solvent is polar which is at least one of water, alcohol including 2-propanol, dimethylformanide, dimethylacetamide, and N-methylpyrrolidinone.

7. The process according to claim 3, wherein said second solvent is at least one of ethyl acetate and hexane.

8. The process according to claim 3, wherein said third solvent is polar which is at least one of water, alcohol including 2-propanol, dimethylformanide, dimethylacetamide, and N-methylpyrrolidinone.

9. The process according to claim 3, wherein said soluble reversible base is at least one of sodium hydroxide, lithium hydroxide, and potassium hydroxide.

10. The process according to claim 3, wherein said soluble non-reversible base is at least one of sodium hydride, lithium hydride, and potassium hydride.

11. A monomer of the structure (IV):

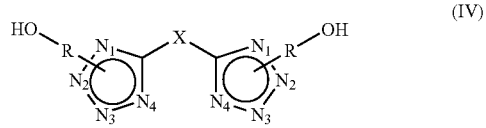

(IV)

wherein "X" is an alkyl group; and wherein "R" is an alkyl group, wherein "R" is chemically bonded to $N_1$ or $N_2$ position.

12. The monomer of the structure (IV) according to claim 11, wherein said monomer of the structure (IV) is a di-tetrazole diol.

13. The monomer of the structure (IV) according to claim 11, wherein said monomer of the structure (IV) is Bis(N-ethanol-5-tetrazolyl)propane, said Bis(N-ethanol-5-tetrazolyl)propane is at least one of 2,2-Bis(5-(1-N-ethanol-5-tetrazolyl)propane of the structure (IVa), 2,2-Bis(5-(2-N-ethanol-5-tetrazolyl)propane of the structure (IVb), and 2-(5-(1-N-ethanol-5-tetrazolyl)-2-(5-(2-N-ethanol-5-tetrazolyl) propane of the structure (IVc);

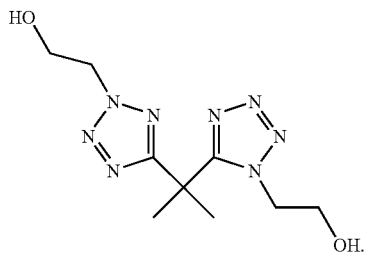

2-(5-(1-N-ethanol-5-tetrazolyl)-2-(5-(2-N-ethanol-5-tetrazolyl)propane

14. The monomer of the structure (IV) according to claim 11, wherein said monomer of the structure (IV) is Bis(N-ethanol-5-tetrazolyl)methane, said Bis(N-ethanol-5-tetrazolyl)methane is at least one of 2,2-Bis(5-(1-N-ethanol-5-tetrazolyl)methane of the structure (IVd), 2,2-Bis(5-(2-N-ethanol-5-tetrazolyl)methane of the structure (IVe), and 2-(5-(1-N-ethanol-5-tetrazolyl)-2-(5-(2-N-ethanol-5-tetrazolyl) methane of the structure (IVf);

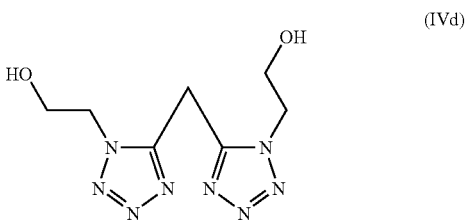

Bis(5-(1-N-ethanol-5-tetrazolyl) methane

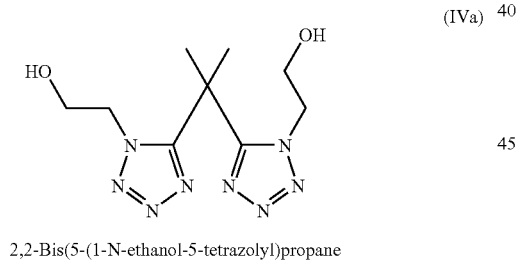

2,2-Bis(5-(1-N-ethanol-5-tetrazolyl)propane

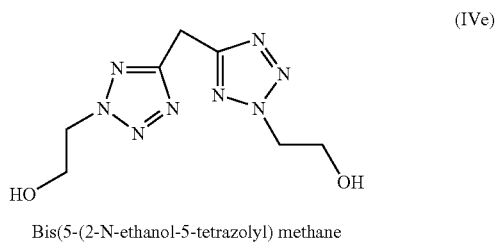

Bis(5-(2-N-ethanol-5-tetrazolyl) methane

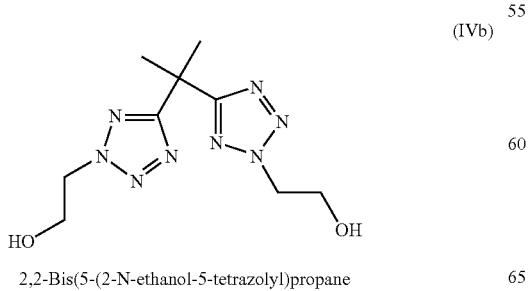

2,2-Bis(5-(2-N-ethanol-5-tetrazolyl)propane

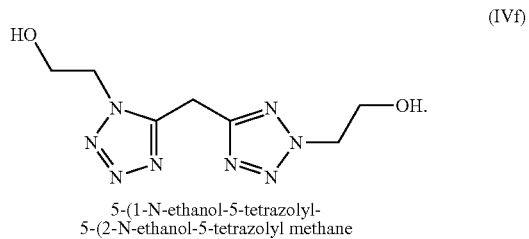

5-(1-N-ethanol-5-tetrazolyl-5-(2-N-ethanol-5-tetrazolyl methane

15. A process for preparing a monomer of the structure (V) comprising:

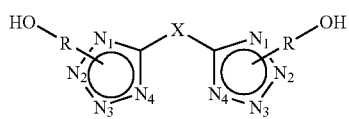

(V)

reacting an effective amount of nitrile(s) with inorganic azide and a divalent zinc salt in a first solvent at about 70° C. to about 170° C. for about 1 hour to about 24 hours, wherein said nitrile(s) are of structure (VI);

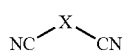

(VI)

wherein "X" is an alkyl group;

cooling to room temperature to obtain a first reaction mixture containing a di-tetrazole of the structure (VII), wherein "H" is chemically bonded to $N_1$ or $N_2$ of position said di-tetrazole, wherein "X" is an alkyl group;

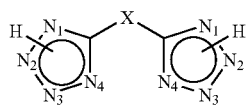

(VII)

recrystallizing or precipitating said di-tetrazole from a second solvent; and reacting an effective amount of said recrystallized di-tetrazole with a soluble reversible or non-reversible base, and 2-chloro-ethanol in a third solvent at about 70° C. to about 150° C. for about 1 hour to about 24 hours;

cooling to room temperature to obtain a second reaction mixture containing a difunctional tetrazole diol of the structure (V), wherein "X" is an alkyl group, wherein "R" is an alkyl group, wherein "R" is chemically bonded to $N_1$ or $N_2$ position of said tetrazole diol (V).

16. The process according to claim 15, wherein said nitrile(s) is at least one of dimethyl-malononitrile and malononitrile.

17. The process according to claim 15, wherein said nitrile(s) is 2,2-dimethyl-malononitrile.

18. The process according to claim 15, wherein said inorganic azide is at least one sodium azide, lithium azide, and potassium azide.

19. The process according to claim 15, wherein said divalent zinc salt is zinc bromide.

20. The process according to claim 15, wherein said first solvent is polar which is at least one of water, alcohol including 2-propanol, dimethylformanide, dimethylacetamide, and N-methylpyrrolidinone.

21. The process according to claim 15, wherein said second solvent is at least one of ethyl acetate and hexane.

22. The process according to claim 15, wherein said third solvent is polar which is at least one of water, alcohol including 2-propanol, dimethylformanide, dimethylacetamide, and N-methylpyrrolidinone.

23. The process according to claim 15, wherein said soluble reversible base is at least one of sodium hydroxide, lithium hydroxide, and potassium hydroxide.

24. The process according to claim 15, wherein said soluble non-reversible base is at least one of sodium hydride, lithium hydride, and potassium hydride.

* * * * *